United States Patent
Leone

(10) Patent No.: US 11,131,645 B2
(45) Date of Patent: Sep. 28, 2021

(54) METHODS AND SYSTEMS FOR HEMATOCRIT MEASUREMENT

(71) Applicant: Trividia Health, Inc., Fort Lauderdale, FL (US)

(72) Inventor: Steven V. Leone, Lake Worth, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 358 days.

(21) Appl. No.: 15/971,636

(22) Filed: May 4, 2018

(65) Prior Publication Data

US 2018/0321179 A1 Nov. 8, 2018

Related U.S. Application Data

(60) Provisional application No. 62/501,861, filed on May 5, 2017.

(51) Int. Cl.
| | |
|---|---|
| *G01N 27/327* | (2006.01) |
| *G01N 33/66* | (2006.01) |
| *C12Q 1/00* | (2006.01) |
| *G01N 33/49* | (2006.01) |

(52) U.S. Cl.
CPC ......... *G01N 27/3274* (2013.01); *C12Q 1/006* (2013.01); *G01N 27/3273* (2013.01); *G01N 33/66* (2013.01); *G01N 27/3272* (2013.01); *G01N 33/49* (2013.01)

(58) Field of Classification Search
CPC ........ G01N 27/02; G01N 27/06; G01N 27/22; G01N 27/028; G01N 27/3274; G01N 27/3272; G01N 27/3273; G01N 33/66; G01N 33/49; G01N 33/39; G01N 33/80; G01N 33/26

See application file for complete search history.

(56) References Cited

U.S. PATENT DOCUMENTS

| | | | |
|---|---|---|---|
| 3,993,948 A | 11/1976 | Epstein | |
| 7,977,112 B2 | 7/2011 | Burke et al. | |
| 8,466,694 B2 * | 6/2013 | Sato .................... | A61B 5/14535 324/692 |
| 2004/0259180 A1 | 12/2004 | Burke et al. | |
| 2008/0200830 A1 | 8/2008 | Pompei | |
| 2009/0038939 A1 | 2/2009 | Popovich et al. | |
| 2011/0073494 A1 | 3/2011 | McColl et al. | |

(Continued)

OTHER PUBLICATIONS

International Search Report in International Application No. PCT/US2018/031180 dated Jul. 23, 2018.

(Continued)

*Primary Examiner* — Gurpreet Kaur
(74) *Attorney, Agent, or Firm* — Greenberg Traurig, LLP; David J. Dykeman; Roman Fayberg

(57) ABSTRACT

Systems and methods for hematocrit measurement are provided. In some embodiments, a method for measuring glucose in a blood sample comprises measuring hematocrit in a blood sample using a Thevenin equivalent circuit to calculate a hematocrit complex impedance value, mapping the calculated hematocrit impedance to a hematocrit concentration in the blood sample, and calculating a concentration of glucose in the blood sampled using the mapped hematocrit concentration.

12 Claims, 14 Drawing Sheets

(56) References Cited

U.S. PATENT DOCUMENTS

| | | | |
|---|---|---|---|
| 2011/0168575 A1* | 7/2011 | Lica | G01N 27/3274 |
| | | | 205/782 |
| 2014/0178909 A1* | 6/2014 | Tonks | C12Q 1/006 |
| | | | 435/14 |
| 2014/0231273 A1* | 8/2014 | McColl | G01N 27/416 |
| | | | 205/792 |
| 2016/0091450 A1 | 3/2016 | McColl et al. | |
| 2017/0082601 A1 | 3/2017 | Cafferty | |

OTHER PUBLICATIONS

Anonymous: "Measuring Resistance, In Circuit and Out—Technical Articles", Retrieved from the Internet:URL:https://www.allaboutcircuits.com/technical-articles/measuring-resistance-in-circuit-and-out/, Jul. 9, 2015.

\* cited by examiner

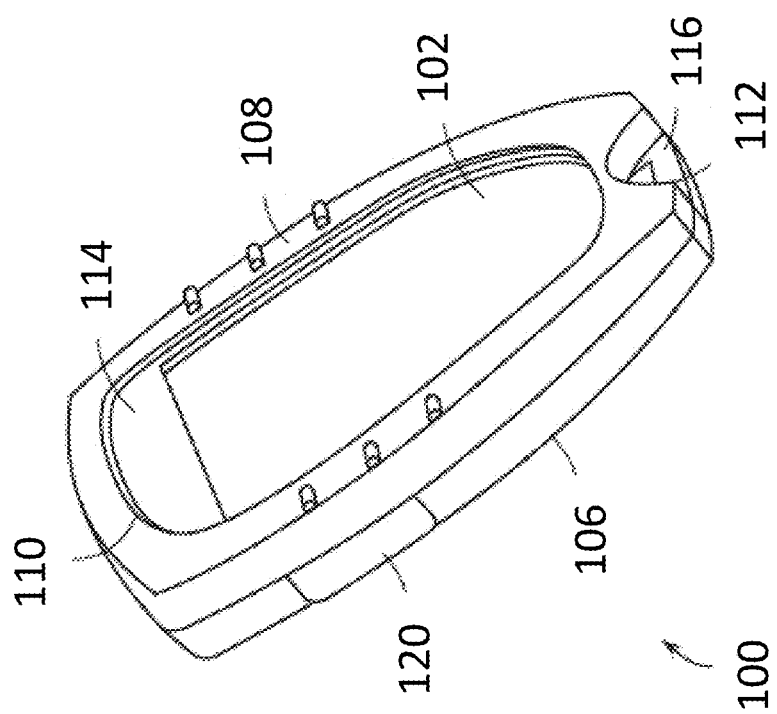

Magnitude HCT Frequency Response

METHODS AND SYSTEMS FOR HEMATOCRIT MEASUREMENT

RELATED APPLICATIONS

The present application claims priority to and the benefit of U.S. Provisional Application No. 62/501,861, filed May 5, 2017, which is incorporated herein by reference in its entirety.

FIELD

The present disclosure relates to systems and methods for hematocrit measurement in connection with blood glucose measurements.

BACKGROUND

Many industries have a commercial need to monitor the concentration of particular constituents in a fluid. In the health care field, individuals with diabetes, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Such systems typically include a test strip where the user applies a fluid sample and a meter that "reads" the test strip to determine the level of the tested constituent in the fluid sample.

SUMMARY

The present disclosure provides systems and methods for hematocrit measurement. In some embodiments, such systems and methods rely on Thevenin impedance method for hematocrit measurement for blood glucose meter.

In some aspects, a method for measuring glucose in a blood sample comprises measuring hematocrit in a blood sample using a Thevenin equivalent circuit to calculate a hematocrit complex impedance value, mapping the calculated hematocrit impedance to a hematocrit concentration in the blood sample, and calculating a concentration of glucose in the blood sampled using the mapped hematocrit concentration. In some embodiments, measuring the hematocrit includes measuring a response current to an excitation voltage. In some embodiments, the response current is inversely proportional to the hematocrit concentration in the blood sample. In some embodiments, the response current is used to calculate the hematocrit complex impedance value. In some embodiments, the calculating the concentration of glucose includes adjusting a measured glucose value using the mapped hematocrit concentration. In some embodiments, the method for measuring glucose in a blood sample further comprises detecting the blood sample for analysis. In some embodiments, an excitation signal is applied to the blood sample such that the response to the excitation signal is analyzed to determine a glucose concentration in the blood sample. In some embodiments, the glucose value is dependent on the mapped hematocrit concentration.

In some aspects, a system for diagnostic testing comprises a test strip, and an electronic meter for performing a diagnostic test on a sample applied to the test strip inserted therein, the electronic meter comprising a housing having a test port for receiving the test strip, and a processor programmed to perform the steps of measuring hematocrit in the sample placed onto a test strip using a Thevenin equivalent circuit to calculate a hematocrit complex impedance value, and mapping the calculated hematocrit impedance to a hematocrit concentration in the blood sample, and calculating a concentration of glucose in the sample using the mapped hematocrit concentration. In some embodiments, measuring the hematocrit includes measuring a response current to an excitation voltage. In some embodiments, the response current is used to calculate the hematocrit complex impedance value. In some embodiments, the calculating the concentration of glucose includes adjusting a measured glucose value using the mapped hematocrit concentration. In some embodiments, an excitation signal is applied to the blood sample such that the response to the excitation signal is analyzed to determine a glucose concentration in the blood sample. In some embodiments, the glucose concentration is dependent on the mapped hematocrit concentration. In some embodiments, the processor is further programmed to detect when the sample is applied to the test strip. In some embodiments, the processor is further programmed to display the adjusted glucose concentration.

In some aspects, a method for measuring glucose in a blood sample comprises detecting a blood sample, measuring hematocrit in the blood sample placed onto a test strip using a Thevenin equivalent circuit to calculate a hematocrit complex impedance value, and mapping the calculated hematocrit impedance to a hematocrit concentration in the blood sample, applying an excitation signal to the blood sample such that the response to the excitation signal is analyzed to determine a glucose concentration in the blood sample, adjusting the glucose concentration in the blood sampled using the mapped hematocrit concentration, and displaying the adjusted glucose concentration. In some embodiments, measuring the hematocrit includes measuring a response current to an excitation voltage. In some embodiments, the response current is inversely proportional to the hematocrit concentration in the blood sample. In some embodiments, the response current is used to calculate the hematocrit complex impedance value.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 2A and 2B illustrate a meter according to some embodiments of the present disclosure;

Figure 1A:
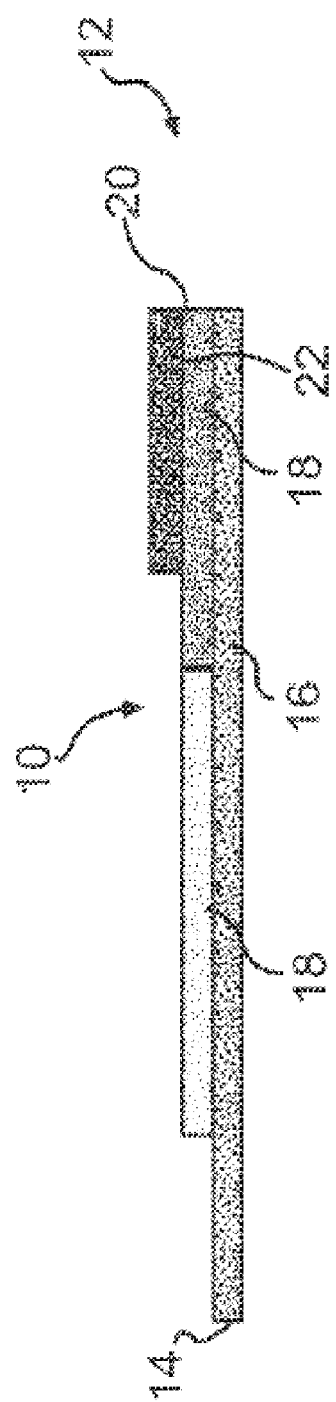
FIG. 1A is a general cross-sectional view of a test strip according to some embodiments of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

The present disclosure provides systems and methods for hematocrit (HCT) measurement. In some embodiments, such systems and methods rely on Thevenin impedance method for HCT measurement for blood glucose meter. In some embodiments, a system and method is provided with a simple way to measure HCT complex impedance for a blood glucose meter using a reference resistor to form a Thevenin equivalent circuit. In order to determine a measurement of an analyte, such as blood glucose, in a sample, such as blood, using a device, such as a blood glucose meter, certain interferents can be accounted for to increase the accuracy of the measurement. For example, one such interferent is the HCT concentration in the blood. In some embodiments, a method of measuring the HCT for a blood glucose meter using a Thevenin equivalent circuit can be used to measure the HCT impedance. The percent of HCT concentration can be mapped to the HCT impedance to measure the concentration of the analyte, such as glucose, in the blood.

A meter for measuring blood glucose or another analyst is a portable, handheld device used to measure blood glucose levels for users with Type I or Type II diabetes. Typically, the user purchases test strips that interface with the meter. The user draws a tiny amount of blood (a few microliters or less) from a finger or other area using a lancer. The strip is inserted into the meter connector port, and the blood droplet is applied onto the exposed end of the strip which has an open port for the blood. A chemical reaction occurs between the blood sample and the chemistry on the strip, which is measured by the meter to determine the blood glucose level in units of mg/dL or mmol/L, depending on regional preferences.

FIG. 1A illustrates a general cross-sectional view of an embodiment of a test strip 10. Test strip 10 includes a proximal end 12, a distal end 14, and is formed with a base layer 16 extending along the entire length of test strip 10. The base layer 16 is preferably composed of an electrically insulating material and has a thickness sufficient to provide structural support to test strip 10. For purposes of this disclosure, "distal" refers to the portion of a test strip further from the fluid source (e.g., closer to the meter) during normal use, and "proximal" refers to the portion closer to the fluid source (e.g., a fingertip with a drop of blood for a glucose test strip) during normal use. The base layer 16 may be composed of an electrically insulating material and has a thickness sufficient to provide structural support to test strip 10.

As seen in FIG. 1A, the proximal end 12 of test strip 10 includes a sample receiving location, such as a sample chamber 20 configured to receive a patient's fluid sample, as described above. The sample chamber 20 may be formed in part through a slot in a dielectric insulating layer 18 formed between a cover 22 and the underlying measuring electrodes formed on the base layer 16. Accordingly, the sample chamber 20 may include a first opening, e.g., a sample receiving location, in the proximal end of the test strip and a second opening for venting the sample chamber 20. The sample chamber 20 may be dimensioned so as to be able to draw the blood sample in through the first opening, and hold the blood sample in the sample chamber 20, by capillary action. The test strip 10 can include a tapered section that is narrowest at the proximal end 12, or can include other indicia in order to make it easier for the user to locate the first opening and apply the blood sample.

Figure 1B:
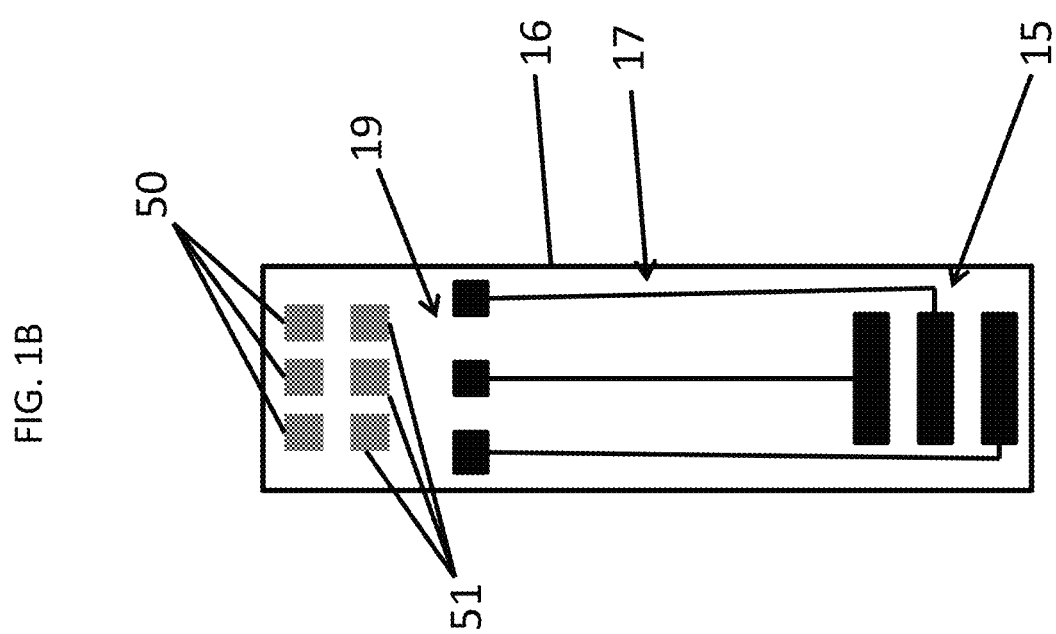
FIG. 1B is a top view of a conductive pattern on a substrate of a test strip according to some embodiments of the present disclosure.

In reference to FIG. 1B, disposed on base layer 16 is a conductive pattern. In some embodiments, the conductive pattern may be formed by laser ablating the electrically insulating material of the base layer 16 to expose the electrically conductive material underneath. Other methods may also be used, such as inserted conductors with physical attachment to control circuit. Other methods may also be used to dispose the conductive pattern on the base layer. The conductive pattern may include a plurality of electrodes 15 disposed on base layer 16 near proximal end 12, a plurality of electrical strip contacts 19 disposed on base layer 16 near distal end 14, and a plurality of conductive traces 17 electrically connecting the electrodes 15 to the plurality of electrical strip contacts 19.

A reagent layer may be disposed on the base layer 16 in contact with at least a working electrode of the conductive pattern. The reagent layer may include an enzyme, such as glucose oxidase, and a mediator, such as potassium ferricyanide or ruthenium hexamine. Reagent layer 90 may also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485). With these chemical constituents, the reagent layer reacts with glucose in the blood sample in the following way. The glucose oxidase initiates a reaction that oxidizes the glucose to gluconic acid and reduces the ferricyanide to ferrocyanide. When an appropriate voltage is applied to working electrode, relative to counter electrode, the ferrocyanide is oxidized to ferricyanide, thereby generating a current that is related to the glucose concentration in the blood sample.

Figure 2A:
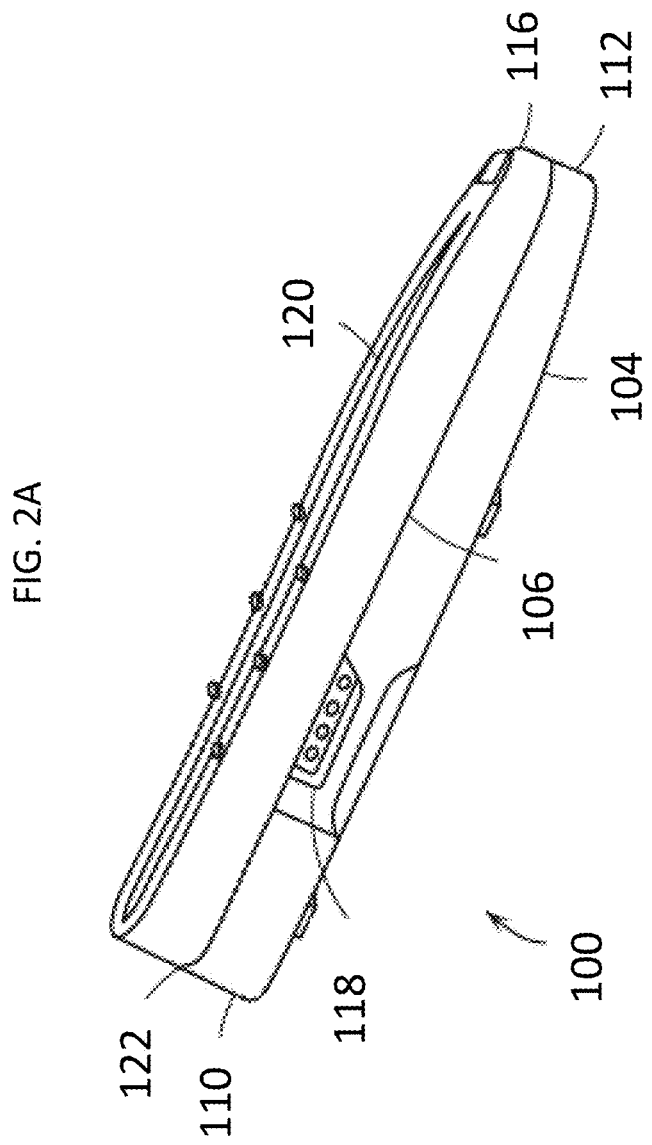

FIG. 2A and FIG. 2B illustrate a meter 100 used to measure the glucose level in a blood sample. The meter 100 includes a housing having a test port for receiving the test strip, and a processor or microprocessor programmed to perform methods and algorithms to determine glucose concentration in a test sample or control solution as disclosed in the present disclosure. In some embodiments, the meter 100 has a size and shape to allow it to be conveniently held in a user's hand while the user is performing the glucose measurement. The meter 100 may include a front side 102, a back side 104, a left side 106, a right side 108, a top side 110, and a bottom side 112. The front side 102 may include a display 114, such as a liquid crystal display (LCD). A bottom side 112 may include a strip connector 116 into which test strip can be inserted to conduct a measurement. The meter 100 may also include a storage device for storing test algorithms or test data. The left side 106 of the meter 100 may include a data connector 418 into which a removable data storage device 120 may be inserted, as necessary. The top side 110 may include one or more user controls 122, such as buttons, with which the user may control meter 100, and the right side 108 may include a serial connector (not shown).

In some embodiments, the blood glucose meter comprises a decoder for decoding a predetermined electrical property, e.g. resistance, from the test strips as information. The decoder operates with, or is a part of, the microprocessor.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user.

A correction based on a measured HCT value can be applied to glucose level determined by the meter. In some embodiments, the HCT measurement sequence begins after a drop of blood or control is detected when the drop completes the circuit between the HCT measurement anode and cathode. In some embodiment, the HCT is analyzed based on an electrical measurement between two electrodes on the test strip separate from the electrodes used to measure glucose, or the electrodes can be shared for both measurements. After the drop is detected an excitation voltage signal is applied to the HCT electrodes. The salt content of blood creates an electronic signature, in which the magnitude and phase response can be mapped to the HCT of the blood. The impedance of the electrical signature is affected by temperature, so the true HCT reading is corrected for temperature for the temperature difference from 24° C. (dT).

In some embodiments, the glucose measurement sequence is initiated only when the meter detects a full sample chamber. The glucose in the test sample is oxidized by the enzyme glucose dehydrogenase-FAD, producing gluconolactone and the reduced form of an electron mediator. The reduced mediator is then oxidized at the surface of the glucose measurement anode to produce an electrical signal (current in nanoamp units) that is detected by the meter. The electrical signal (current, in nanoamps) produced by oxidation of the reduced mediator at the surface of the glucose measurement anode is proportional to the amount of glucose in the test sample. The HCT value (which can be temperature corrected) is then used to determine the temperature corrected glucose value.

The meter can measure blood glucose by analyzing the electrical response to an excitation signal. However, this response is dependent on the HCT concentration in the blood. The accuracy of the glucose measurement is therefore dependent on the accuracy of the HCT concentration to compensate the measurement for this interferent. For a given blood glucose sample, the response current to a voltage excitation used to measure blood glucose on the blood sample can be inversely proportional to the HCT concentration in the blood. Knowing the HCT impedance provides the data to map the HCT concentration to the impedance through empirical methods. This known HCT concentration (% HCT), can then be used to provide an accurate blood glucose measurement.

Various methods can be used for measuring the HCT concentration from step response to impedance measurement. In some embodiments, a method of measuring the HCT for a blood glucose meter using a Thevenin equivalent circuit can be used to measure the HCT impedance.

Figure 3:
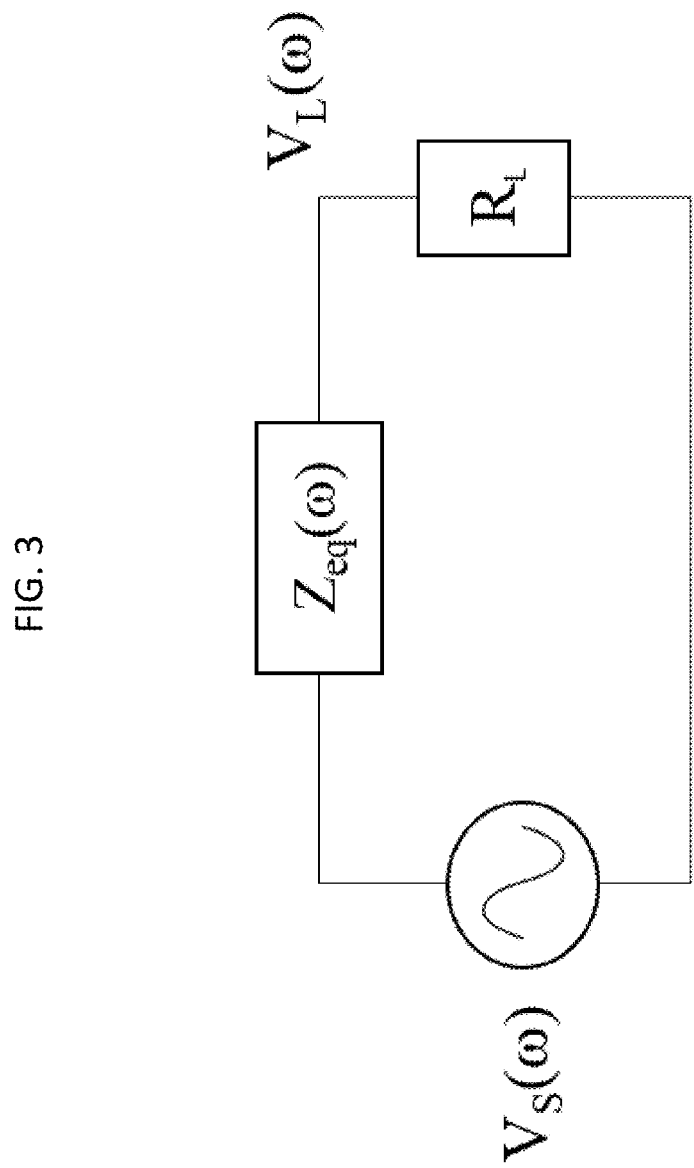
FIG. 3 is an exemplary circuit with an equivalent resistance showing the Thevenin method configuration.
Figure 4:
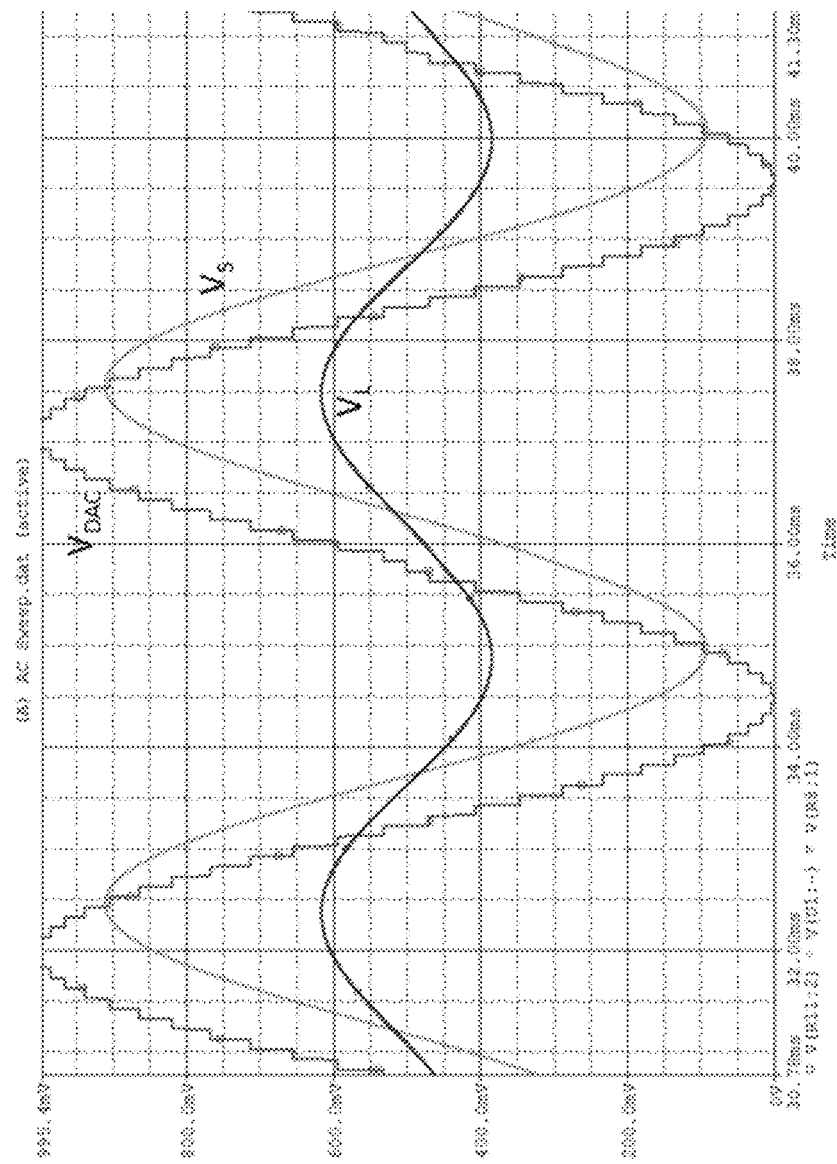
FIG. 4 is an embodiment of a sample generated digital excitation, analog low pass filtered excitation applied to the impedance VS, and response signal VL.

FIG. 3 illustrates an embodiment of features to implement the Thevenin equivalent method to measure HCT in a blood glucose meter. For example, this can include a sinusoidal excitation source $V_S(\omega)$, and a resistive reference $R_L$. In some embodiments, to generate a sinusoidal excitation would be to generate a step-wise sinusoidal approximation with a digital to analog converter (DAC) as shown in FIG. 4 ($V_{DAC}$). Then a low pass filter can be used to generate a smooth excitation signal $V_S$. The strip electrodes could be the same as is currently used for HCT, not necessarily involving any applied chemistry.

It is known that a first order HCT equivalent circuit model can be shown to be configured as a combination of resistors and a capacitor as shown below. Higher order approximations will have additional energy storage inductive and capacitive components, but this is the simplest for discussion. The equivalent circuit impedance is frequency dependent due to the presence of the capacitor.

$Z_{eq}(\omega)$ =>

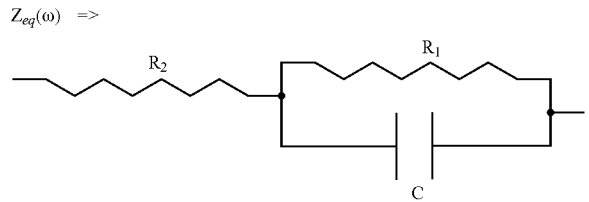

Figure 5:
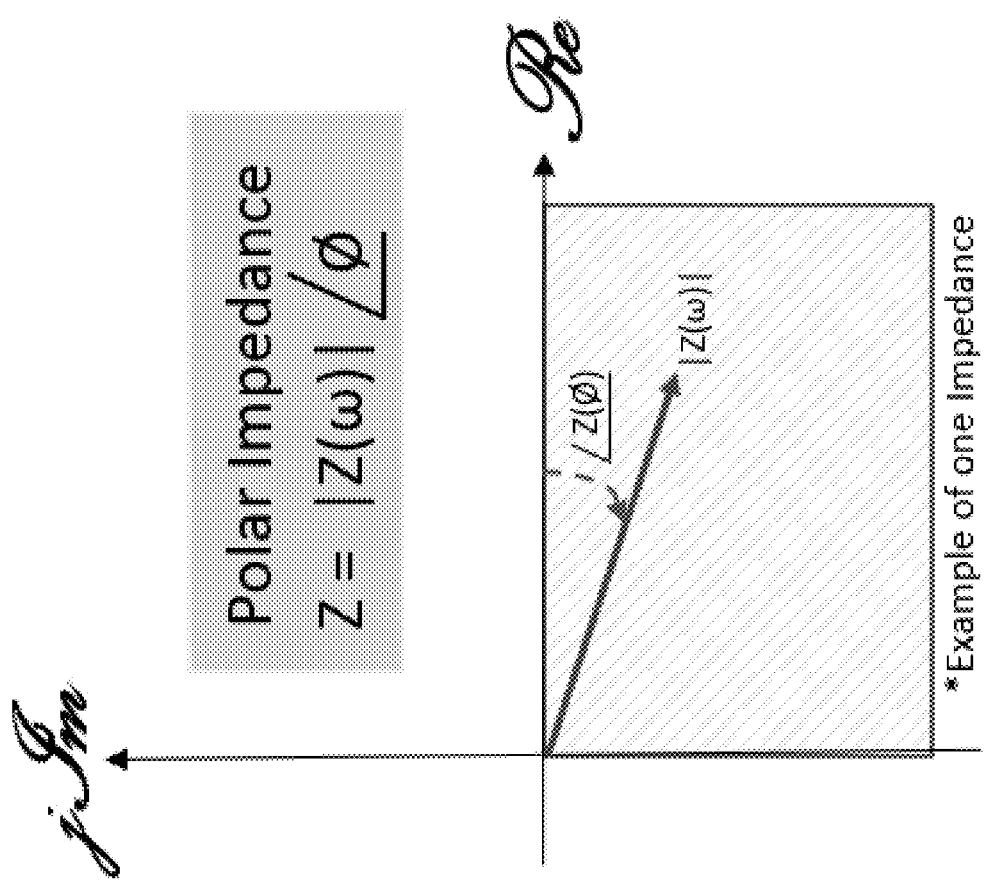
FIG. 5 is a graph showing an exemplary plot of complex impedance.

The frequency dependent impedance $Z_{eq}(\omega)$, for this and more complex models, can be represented as a complex number;

$\mathcal{Re} + j\mathcal{Im}$ composed of a real part and an imaginary part. $\omega$ is the radian frequency. This number can also be interchanged to the polar coordinate system to be represented as a vector $|Z_{eq}(\omega)| \angle \varnothing$ where, $|Z_{eq}(\omega)|$ is the magnitude and $\angle \varnothing$ is the phase angle of the complex impedance. An exemplary plot of impedance on the real and imaginary axes is shown in FIG. 5. Other passive components can be added to better approximate the equivalent circuit model but any modification will still result in the same complex representation format.

In some embodiments, an unknown impedance can be measured by exciting the impedance with a known sinusoidal excitation (amplitude and frequency) $V_S(\omega)$, and dividing the output with a known precision resistor $R_L$ and measuring the response $V_L(\omega)$, as shown in FIG. 3.

Using this method, the equivalent unknown impedance magnitude can be shown to be $$|Z_{eq}| = R_L\left(\frac{V_S}{V_L} - 1\right)$$

where $V_S$ and $V_L$ represent the amplitudes of the respective sinusoidal signals $V_S(\omega)$ and $V_L(\omega)$. This is known as a Thevenin equivalent impedance measurement.

The phase angle $\angle \varnothing$ can be measured as the phase difference between $V_S(\omega)$ and $V_L(\omega)$.

Figure 6:
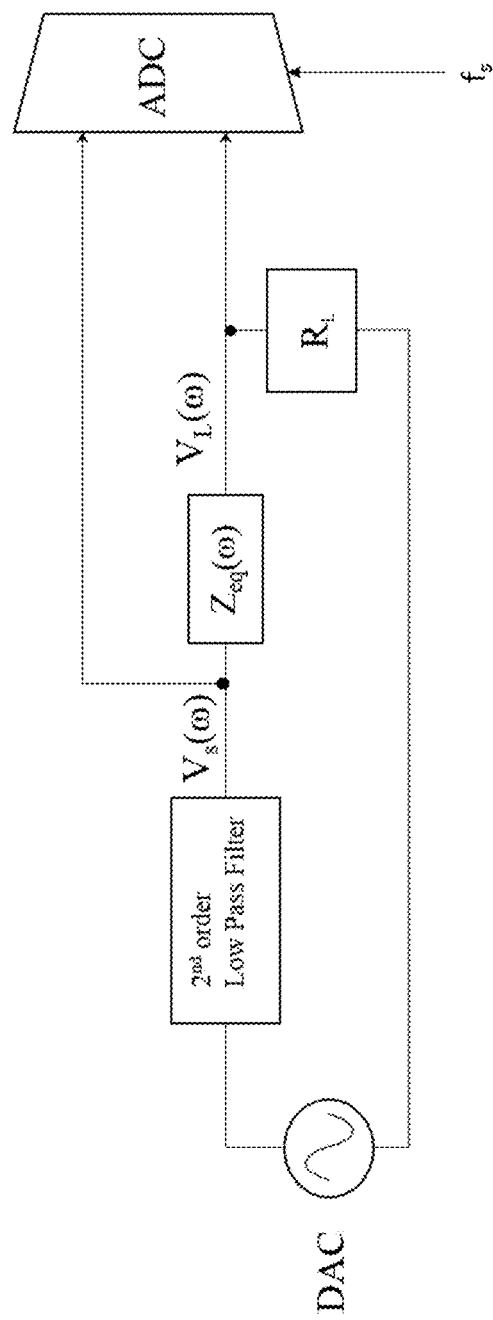
FIG. 6 is an exemplary block diagram for hematocrit identification using Thevenin method.

A sample excitation and response is shown in FIG. 4. In this embodiment, the excitation signal is generated with a Digital to Analog converter (DAC), at a rate sufficiently higher than the excitation frequency, which has a stepwise response as shown in FIG. 6. An active low pass filter can be used to remove the higher frequencies of the DAC generated sinusoid to provide a pure sinusoidal frequency free of spurious harmonics.

A practical implementation of this system is shown in FIG. 6. The sinusoidal excitation is generated with a DAC at the frequency chosen to provide optimum HCT identification. Then this signal is filtered to generate a smooth excitation signal which is measured by the ADC and fed to the HCT sample. The response signal is also simultaneously measured by the ADC. The ADC must have a high enough sample rate $f_S$ such that it can accurately measure the peak amplitude of the excitation and response, as well as the phase difference.

In some embodiments, the phase angle is measured as the difference in time between the zero crossing of the the excitation signal and the zero crossing of the response. This can be done with the ADC, provided the sample rate is fast enough. From the time difference $\Delta T$, at a given frequency, the phase angle is calculated as follows:

$$\varnothing = f_S(\Delta T)360°$$

where $\varnothing$ is the phase angle in degrees, $f_S$ is the ADC sample rate (Hz), and $\Delta T$ is the time differnce between excitation and response signals zero crossing. For example, the "zero crossing" is the time when the exciation or response passes the mid point, which may or may not be zero. This time can be measured by the number of sample points between the zero crossings of the excitation and response. Since the sample frequency is known, the time difference is the sample period multiplied by a number of samples between zero crossings.

Figure 7:
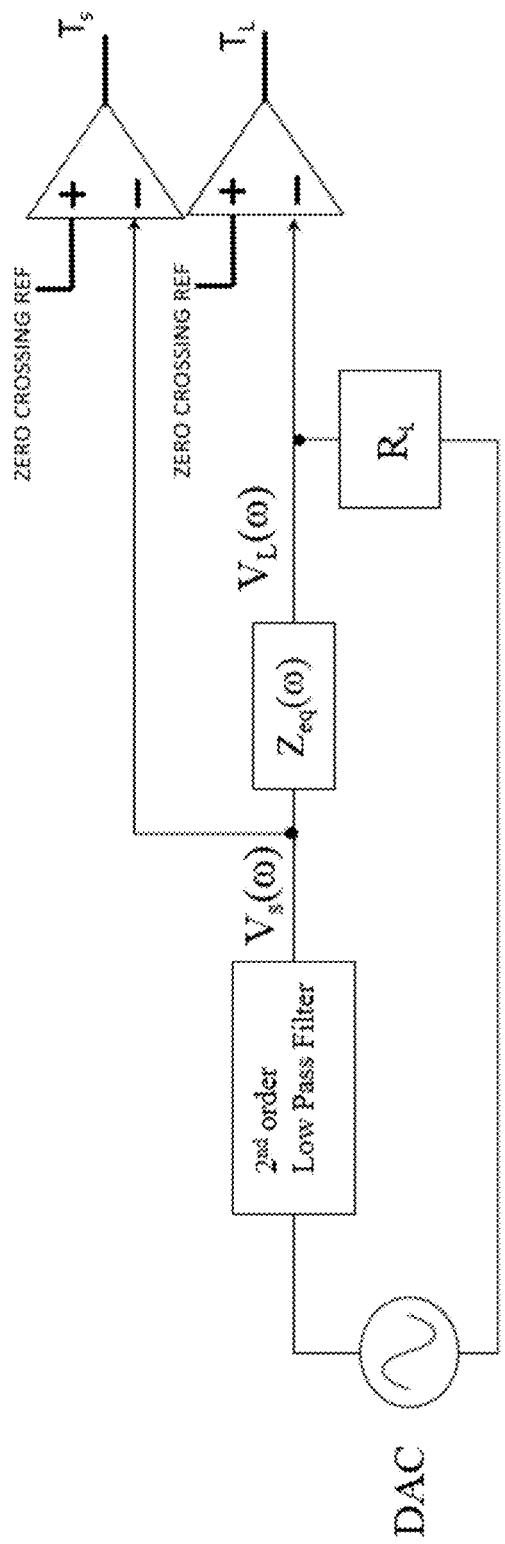
FIG. 7 is an exemplary block diagram for an embodiment of an alternate method for measuring a phase angle of an complex impedance for hematocrit identification.
Figure 8:
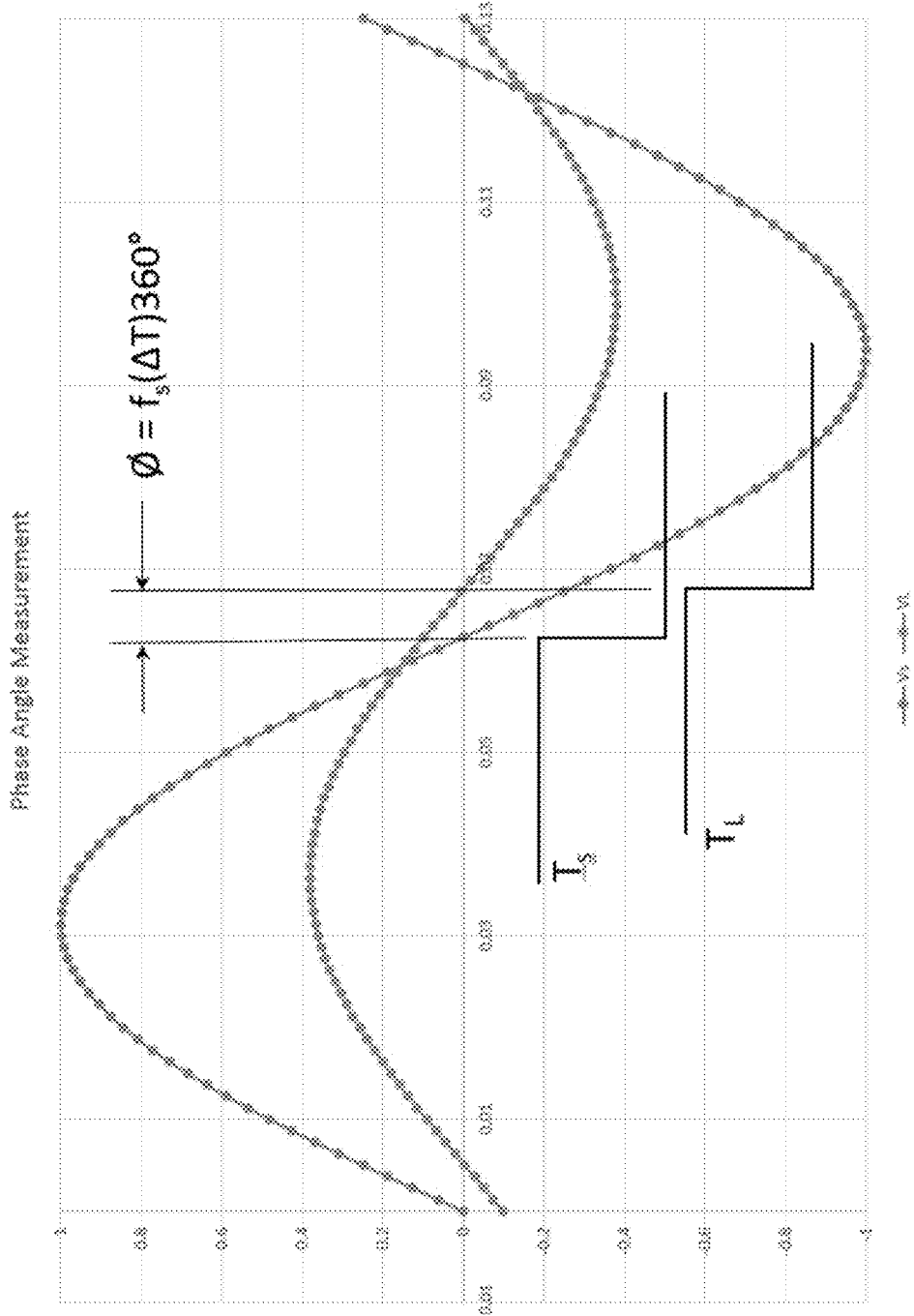
FIG. 8 is an exemplary graph showing a measuring and computation for phase angle as the time difference between the zero (mid-point) crossing between the excitation and the response signals.

In some embodiments, the phase angle can be measured with a pair of comparators with the references set to the mid point, zero crossing, as shown in FIG. 7. The comparator digital outputs each being tied to input capture timer registers to compute an accurate time difference, as shown in FIG. 8. In some embodiments, these comparators already exist in the mixed signal microcontroller.

Figure 9:
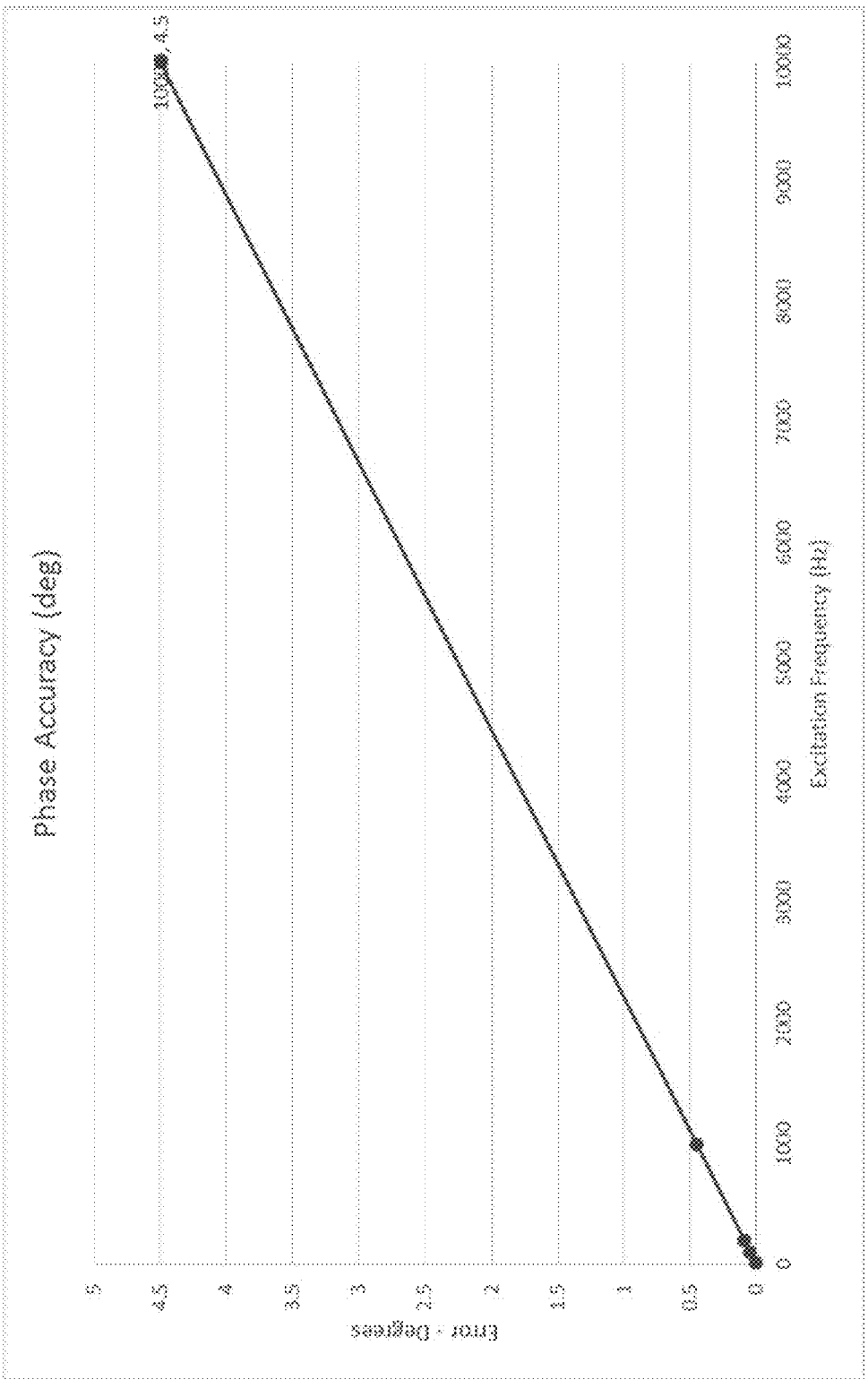
FIG. 9 is a plot of the error in phase accuracy being proportional to excitation frequency.

The accuracy of the phase angle is proportional to the ADC sample rate as more points between zero crossings gives better accuracy. It is also inversely proportional to the excitation frequency as shown in the error table in FIG. 9, which illustrates the way in which error is proportional to frequency (accuracy inversely proportional to frequency).

Figure 10:
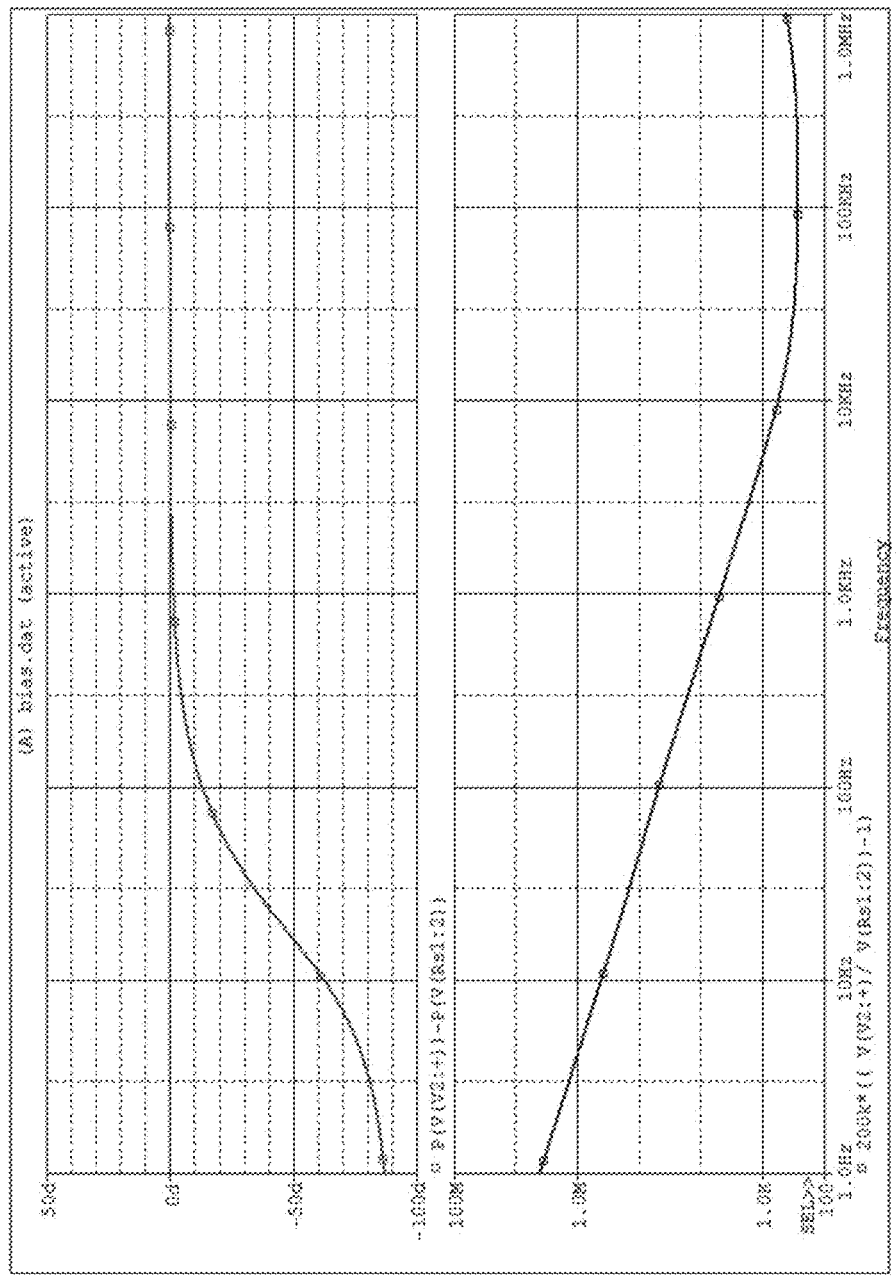
FIG. 10 is an exemplary graph of complex impedance magnitude and phase angle as a function of frequency.

Impedance is a function of frequency. In some embodiments, an excitation frequency is chosen that suits the range of possibilities. For example, an excitation frequency of 8 Hz can be chosen to provide a good measure of impedance accuracy, as a larger phase difference can be expected than at, for example, 1.0 kHz (see FIG. 10). In some embodiments, an excitation frequency can be chosen that both provides for good accuracy (low excitation frequency/high ADC sample rate) but not so low that a high sample rate ADC will overflow the ADC counter (for example, a 16 bit counter) in the sample window selected. A good choice of excitation frequency can be one that shows linearity in the magnitude and phase response around the excitation frequency and does not saturate (the slope approach zero or infinity).

Figure 11:
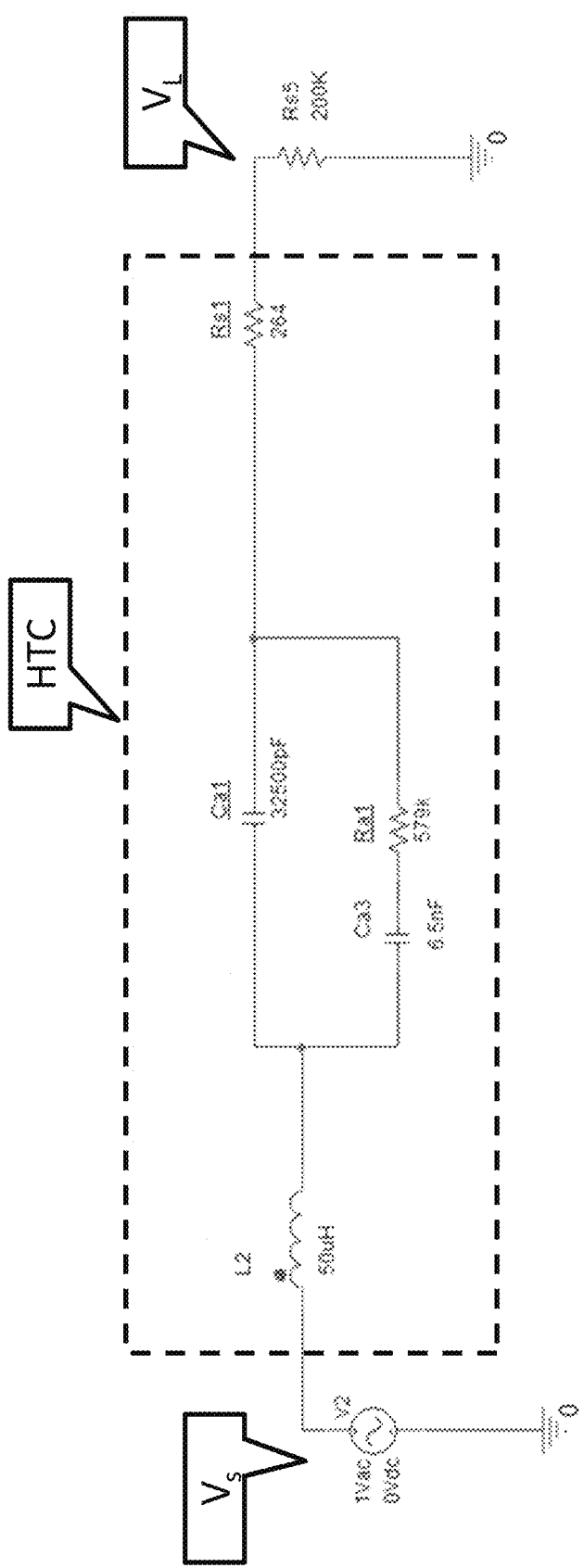
FIG. 11 is an embodiment of a hematocrit impedance modelling system including a pure sinusoidal excitation, an LRC impedance model for hmatocrit, and a reference resistance $R_L$.
Figure 12:
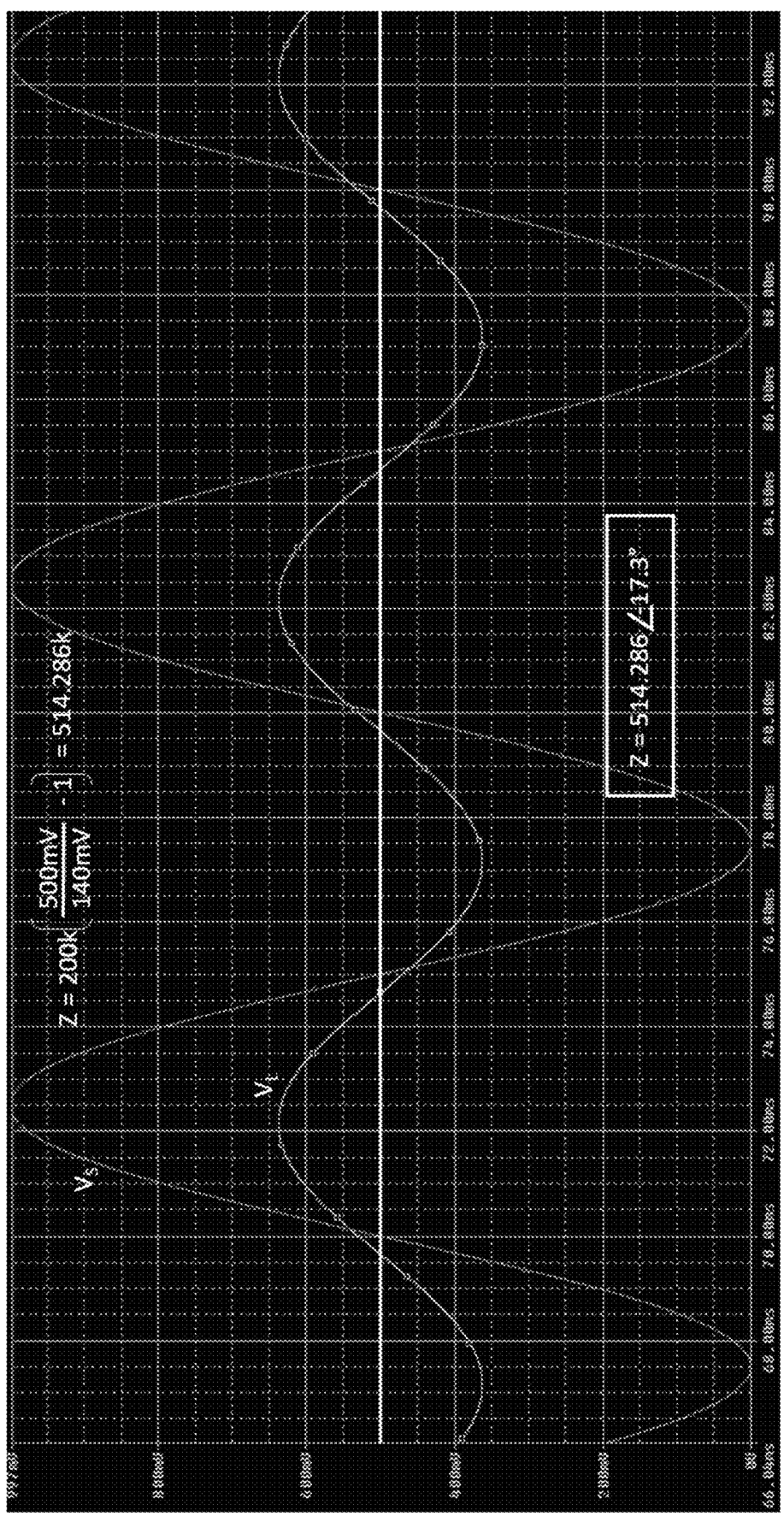
FIG. 12 is an exemplary graph of an example excitation VS and response VL and the associated impedance magnitude calculation.

Referring to FIG. 11, an embodiment of a HCT impedance model and measurement is shown. FIG. 11 shows an embodiment of a circuit model implementation of the Thevenin method for impedance measurement with the sinusoidal excitation frequency, additional lumped parameter components such as contract resistance, the sample HCT equivalent circuit model (which will be across two strip electrodes), and the precision reference resistor. Not shown in FIG. 11 is an ADC, DAC or low pass filter, and any comparators inputs. FIG. 12 shows an example excitation, $V_S$ and response, $V_L$ and the associated impedance magnitude calculation and phase representation. This is an example of what can be generated to estimate percent HCT concentration. In other words, $|Z|\angle\emptyset=514.286\angle-17.3°$. The 0.5V DC offset source represents that the signal generated is offset by a DC level to make the measurements compatible with low cost battery operated microcontroller based systems.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure.

What is claimed is:

1. A method for measuring glucose in a blood sample, comprising:
    measuring a glucose response current generating by an excitation voltage applied to a glucose electrode on a test strip for measuring a glucose concentration in the blood sample;
    generating a second excitation voltage using a digital to analog converter and passing the second excitation voltage through a low pass filter to remove higher frequencies to provide a pure sinusoidal frequency;
    measuring a hematocrit response current generated by the second excitation voltage applied to a hematocrit electrode on the test strip for measuring hematocrit in a blood sample, the measured hematocrit response current being used with a Thevenin equivalent circuit to calculate a hematocrit complex impedance value;
    mapping the calculated hematocrit complex impedance value to a hematocrit concentration in the blood sample;
    correcting the measured glucose concentration in the blood sampled using the mapped hematocrit concentration.

2. The method of claim 1, wherein the hematocrit response current is inversely proportional to the hematocrit concentration in the blood sample.

3. The method of claim 1, further comprising detecting the blood sample for analysis.

4. The method of claim 1, wherein the glucose concentration is dependent on the mapped hematocrit concentration.

5. A system for diagnostic testing comprising:
    a test strip; and
    an electronic meter for performing a diagnostic test on a sample applied to the test strip inserted therein, the electronic meter comprising:
        a housing having a test port for receiving the test strip, and
        a processor programmed to perform the steps of:
            measuring hematocrit in the sample placed onto the test strip using a Thevenin equivalent circuit to calculate a hematocrit complex impedance value; and
            mapping the calculated hematocrit complex impedance value to a hematocrit concentration in the sample; and
            adjusting a concentration of glucose in the sample using the mapped hematocrit concentration
            wherein measuring the hematocrit includes measuring a response current to an excitation voltage, the excitation voltage being generated by a digital to analog converter and being passed through a low pass filter to remove higher frequencies to provide a pure sinusoidal frequency, the measured response current being used to calculate the hematocrit complex impedance value.

6. The system of claim 5, wherein an excitation signal is applied to the sample such that the response to the excitation signal is analyzed to determine a glucose concentration in the sample.

7. The system of claim 6, wherein the glucose concentration is dependent on the mapped hematocrit concentration.

8. The system of claim 5, wherein the processor is further programmed to detect when the sample is applied to the test strip.

9. The system of claim 5, wherein the processor is further programmed to display the adjusted glucose concentration.

10. A method for measuring glucose in a blood sample, comprising:
    detecting a blood sample;
    generating a hematocrit excitation voltage using a sinusoidal excitation source in the form of a digital to analog converter and passing the hematocrit excitation voltage through a low pass filter to remove higher frequencies to provide a pure sinusoidal frequency;
    measuring hematocrit in the blood sample placed onto a test strip by measuring a hematocrit response current generated by the hematocrit excitation voltage applied to a hematocrit electrode on the test strip using a Thevenin equivalent circuit to calculate a hematocrit complex impedance value, the Thevenin equivalent circuit including the sinusoidal excitation source for the hematocrit excitation voltage and a reference resistor;
    mapping the calculated hematocrit complex impedance value to a hematocrit concentration in the blood sample;
    applying an excitation signal to the blood sample such that a response to the excitation signal is analyzed to determine a glucose concentration in the blood sample;
    adjusting the glucose concentration in the blood sampled using the mapped hematocrit concentration; and
    displaying the adjusted glucose concentration.

11. The method of claim 10, wherein the hematocrit response current is inversely proportional to the hematocrit concentration in the blood sample.

12. A system for diagnostic testing comprising:

a test strip; and an electronic meter for performing a diagnostic test on a sample applied to the test strip inserted therein, the electronic meter comprising:

a housing having a test port for receiving the test strip, and a processor programmed to perform the steps of:

measuring a hematocrit response current generated by an excitation voltage applied to a hematocrit electrode on the test strip, the measured hematocrit response current being used with a Thevenin equivalent circuit to calculate a hematocrit complex impedance value, the Thevenin equivalent circuit including a sinusoidal excitation source in the form of a digital to analog converter for the excitation voltage and being passed through a low pass filter to remove higher frequencies to provide a pure sinusoidal frequency and a reference resistor; and mapping the calculated hematocrit complex impedance value to a hematocrit concentration in the blood sample; and calculating a concentration of glucose in the sample and correcting the calculated concentration of glucose using the mapped hematocrit concentration.

* * * * *